United States Patent
Alper et al.

(10) Patent No.: US 10,467,718 B2
(45) Date of Patent: Nov. 5, 2019

(54) METHOD FOR DETERMINING BENCHMARKS FOR HAND PRODUCT USE AND COMPLIANCE

(71) Applicant: DebMed USA LLC, Charlotte, NC (US)

(72) Inventors: Paul Alper, Brookline, MA (US); John Hines, Cheshire (GB); Dean Philip Limbert, Derby Derbyshire (GB); Bryan George Frank Anderson, Windsor (GB)

(73) Assignee: DEB IP LIMITED (GB)

( * ) Notice: Subject to any disclaimer, the term of this patent is extended or adjusted under 35 U.S.C. 154(b) by 922 days.

(21) Appl. No.: 13/926,864

(22) Filed: Jun. 25, 2013

(65) Prior Publication Data

US 2013/0290016 A1    Oct. 31, 2013

Related U.S. Application Data

(63) Continuation-in-part of application No. 13/669,988, filed on Nov. 6, 2012, now Pat. No. 10,277,868.

(Continued)

(51) Int. Cl.
*H04B 7/24* (2006.01)
*G06Q 50/22* (2018.01)
*G06Q 10/06* (2012.01)

(52) U.S. Cl.
CPC .......... *G06Q 50/22* (2013.01); *G06Q 10/063* (2013.01); *G06Q 10/06393* (2013.01); *Y02A 90/22* (2018.01); *Y02A 90/26* (2018.01)

(58) Field of Classification Search
CPC ........ G06F 19/322; A61K 6/00; G06Q 50/22; G06Q 50/24; G06Q 40/08; G06Q 10/10
See application file for complete search history.

(56) References Cited

U.S. PATENT DOCUMENTS 5,945,910 A    8/1999   Gorra
6,062,421 A *  5/2000   Marley ................... A47F 1/04
                                                     221/45

(Continued)

FOREIGN PATENT DOCUMENTS

WO    2003082351    10/2003
WO    2005093681    10/2005

OTHER PUBLICATIONS

Boyce, John M., et al., "Evaluation of an Electronic Device for Real-Time Measurement of Alcohol-Based Hand Rub Use," Infection Control and Hospital Epidemiology, Nov. 2009, vol. 30, No. 11, 6 pages.

(Continued)

*Primary Examiner* — Howard D Brown, Jr.
(74) *Attorney, Agent, or Firm* — McAndrews, Held & Malloy, Ltd.

(57) ABSTRACT

A hand product use benchmark is determined for a target institution based on observations of hand product use in a studied institution and relationships between the number of observed hand product uses and characteristics of the studied institution. The benchmark for the target institution is determined based on target institution characteristics and the relationships between institution characteristics and observed hand product uses of the studied institution. The benchmark for the target institution may be adjusted based on direct observation of hand product uses in the target institution and based on actual conditions on which the benchmark is based. Compliance with the benchmark is determined by comparison of activity within the target institution to the benchmark.

15 Claims, 2 Drawing Sheets

Related U.S. Application Data

(60) Provisional application No. 61/556,680, filed on Nov. 7, 2011.

(56) References Cited

U.S. PATENT DOCUMENTS

| | | | |
|---|---|---|---|
| 6,125,482 | A | 10/2000 | Foster |
| 6,236,317 | B1 | 5/2001 | Cohen et al. |
| 6,236,953 | B1 | 5/2001 | Segal |
| 6,392,546 | B1 | 5/2002 | Smith |
| 6,404,837 | B1 | 6/2002 | Thompson et al. |
| 6,577,240 | B2 | 6/2003 | Armstrong |
| 7,242,307 | B1 | 7/2007 | LeBlond et al. |
| 7,271,728 | B2 | 9/2007 | Taylor et al. |
| 7,372,367 | B2 | 5/2008 | Lane et al. |
| 7,682,464 | B2 | 3/2010 | Glenn et al. |
| 7,783,380 | B2 | 8/2010 | York et al. |
| 2001/0054038 | A1 | 12/2001 | Crevel et al. |
| 2002/0135486 | A1 | 9/2002 | Brohagen et al. |
| 2004/0001009 | A1 | 1/2004 | Winings et al. |
| 2007/0008146 | A1 | 1/2007 | Taylor et al. |
| 2007/0083385 | A1* | 4/2007 | Patterson ........... G06Q 10/0639 705/2 |
| 2007/0182571 | A1 | 8/2007 | Kennish et al. |
| 2007/0229288 | A1 | 10/2007 | Ogrin et al. |
| 2009/0189759 | A1 | 7/2009 | Wildman et al. |
| 2010/0094581 | A1 | 4/2010 | Cagle |
| 2010/0153374 | A1* | 6/2010 | LeBlond .......... G06Q 10/06398 707/722 |
| 2010/0173581 | A1* | 7/2010 | Dolan ................... G07C 1/10 455/39 |
| 2010/0188228 | A1 | 7/2010 | Hyland |
| 2013/0113931 | A1* | 5/2013 | Alper ................... H04N 7/18 348/143 |
| 2013/0342349 | A1* | 12/2013 | Cruz ................... G08B 21/245 340/573.1 |

OTHER PUBLICATIONS

Boyce, John M., et al., "Guideline for Hand Hygiene in Health-Care Settings," Morbidity and Mortality Weekly Report, Oct. 25, 2002, vol. 51, No. RR-16.

Crosby, Cynthia T., "Hand hygiene: are we doing better? (Infection Protection)," Heathcare Purchasing News, Dec. 1, 2005, pp. 1-3, HighBeam Research.

Deb Group Ltd., "Hand Hygiene: A Simple Cost-Effective Weapon in the Fight against Healthcare-Associated Infections," www.debgroup.com, Feb. 24, 2011, 2 pages.

Desorbo, Mark A., "Hands for Hygiene," Food Quality, Apr./May 2005, 5 pages.

Doty, Laura, "Food Safety: Helping Hands," Foodservice Equipment & Supplies, Mar. 1, 2005, 4 pages.

"Employee and Health and Personal Hygiene Handbook," FDA, Dec. 1, 2009, pp. 1-64.

Larson, Elaine L. et al., "Hand Hygiene Behavior in a Pediatric Emergency Department and a Pediatric Intensive Care Unit: Comparison of Use of 2 Dispenser Systems," American Journal of Critical Care (AJCC), Jul. 2005, vol. 14, No. 4, pp. 304-311.

Lazarus, Ian R. et al., "Providers, Payers and IT Suppliers learn it pays to GET LEAN'," Managed Healthcare Executive, Feb. 2006, 4 pages.

Lazarus, Ian R., et al., "Six Sigma Raising the Bar," Managed Healthcare Executive, Jan. 2003, pp. 1-4.

Lazarus, Ian R., et al., "Six Signma Enters the Healthcare Mainstream," www.creative-healthcare.com, 2004, 5 pages.

Lindqvist, Peter, "RFID Monitoring of Heath Care Routines and Processes in Hospital Environment," Abstract of Master's Thesis, Helsinki University of Technology, Jul. 28, 2006, pp. 1-82.

Matthews, Mark R., "A Legacy for Leaders: Opportunities in Six Sigma and Lean for Healthcare Providers & Suppliers," www.creative-heathcare.com, 2005, pp. 1-204.

"DPAC Technologies to Showcase OEM Implementation of Airborne Wireless LAN Node Module at the Medical Design & Manufacturing Conference and Expo," Business Wire, Jan. 5, 2004, 2 pages, HighBeam Research.

Morgan, Dennis A., et al., "A Computer Software Application for Managing Occupational Exposure Data," American Industrial Hygiene Association Journal, vol. 59, No. 10; Oct. 1998, pp. 723-728.

Perlik, Allison, "Keeping Safety in Hand," Restaurants & Institutions, Apr. 1, 2001, 2 pages.

Pittel, Didier, "Improving Adherence to Hand Hygiene Practice: A Multidisciplinary Approach," Emerging Infectious Diseases, vol. 7, No. 2, Mar.-Apr. 2001, pp. 234-240.

Sax, Hugo, et al., "The World Health Organization Hand Hygiene Observation Method," www.ajicjournal.org, Sep. 30, 2009, pp. 1-8.

Stedd, Sue, "Cognos Systems Announces i-Hygiene™ Reducing Risk Associated with Hand Hygiene for Healthcare and Food Service Operations," www.cognos-systems.com, Mar. 17, 2006, 2 pages.

Steed, Connie, et al., "Hospital Hand Hygiene Opportunities: Where and when (HOW2)? The HOW2 Benchmark Study," American Journal of Infection Control, vol. 39, No. 1, Feb. 2011, pp. 19-26.

"iHygiene: Wireless Monitoring of Hand Hygiene Compliance," Woodward Laboratories Product Literature, 2 pages.

Leblond, Claude, "Woodward Laboratories Announces the Release of iHygiene," Woodward Laboratories Press Release, Jan. 4, 2004, 2 pages.

Observation Form, "Patient Safety: Save Lives," World Health Organization, revised Aug. 2009, 4 pages.

World Health Organization, "WHO Guidelines on Hand Hygiene in Health Care (Advanced Draft): A Summary," Geneva, Switzerland, World Health Organization 2005, pp. 1-31.

World Health Organization, "WHO Guidelines on Hand Hygiene in Health Care (Advanced Draft): Global Patient Safety Challenge 20005-2006: Clean Care is Safer Care," Apr. 2006, pp. 1-209.

PCT, Notification of Transmittal of the International Search Report and the written Opinion of the International Searching Authority, or the Declaration, in Application No. PCT/US2012/063697, dated Jan. 31, 2013 (12 pages).

PCT, Notification Concerning Transmittal of International Preliminary Report on Patentability, in Application No. PCT/US2012/063697, dated Oct. 9, 2014 (6 pages).

European Patent Office, Communication with extended European search report, in Application No. 12846835.2, dated Jul. 16, 2015 (4 pages).

Office Action dated Sep. 21, 2016 of Chinese Patent Application No. 2012800661677, filing date Nov. 6, 2012, 7 pages.

\* cited by examiner

METHOD FOR DETERMINING BENCHMARKS FOR HAND PRODUCT USE AND COMPLIANCE

CROSS REFERENCE TO RELATED APPLICATIONS

This application is a continuation in part of U.S. patent application Ser. No. 13/669,988, filed Nov. 6, 2012, which claims the benefit of U.S. Provisional Patent Application No. 61/556,680, filed Nov. 7, 2011. The contents of those prior applications are incorporated herein by reference, in their entirety.

BACKGROUND OF THE INVENTION

Many work activities require use of products for protection and/or health of a worker's hands and/or for safe performance of work activities. Such hand products include hand hygiene products to prevent spread of contamination or disease, pre-work or barrier creams to protect hands, hand washing products, skin care products to maintain skin health and prevent occupational dermatitis and gloves for hand protection. The invention concerns determining the compliance by workers with best practices for hand product use.

Hand hygiene is essential for certain activities and services, including particularly healthcare and food preparation and service. For healthcare providers, the spread of healthcare acquired infections also known as HAI's has been an ever increasing challenge in healthcare facilities. HAIs can result from transmission of bacteria, viruses and other disease causing micro-organisms from various sources such as a patient or environmental surfaces to another patient or surface via the hands of healthcare workers. Such transmission can result in an infection of a patient who was previously not infected. Health care facilities have battled MRSA (methicillin-resistant *Staphylococcus aureus*) and VRSA (vancomycin-resistant *Staphylococcus aureus*) and other drug resistant micro-organisms for many years. These problems have been more apparent in recent years. It is estimated that approximately 2,000,000 such HAIs occur annually in the U.S. alone resulting in about 100,000 deaths. The extra costs associated with these infections are estimated in the billions of dollars.

Healthcare institutions seek to prevent and control the spread of HAIs. One important aspect of such efforts is seeking to ensure that health care professionals comply with hand hygiene best practices. Hand hygiene can be accomplished by washing hands with soap and water and by using liquids such as a sanitizing product which does not require water or rinsing of the product.

Hand hygiene is also recognized as essential in the food industry to prevent the spread of foodborne bacteria and/or viruses including Norovirus, the Hepatitis A virus, *Salmonella Typhi*, *Shigella* spp., and *Escherichia coli* (*E. coli*) O157:H7 or other Enterohemorrhagic or Shiga toxin-producing *E. coli*, *Staphylococcus aureus*, *Salmonella* spp. and *Streptococcus pyogenes*. Hand washing by food employees is essential after activities that contaminate hands and before activities during which pathogens may be spread to food.

Exposure to harmful substances in work environments may lead to irritant or allergic contact dermatitis. Continuous wet working conditions may also lead to dermatitis. The cost of occupational dermatitis is difficult to estimate but is clearly substantial both in lost productivity and treatment. Blankiforti, L., *Economic Burden of Dermatitis in US Workers*, 52 JOEM No. 11 1045-54 (2010). Skin care products can maintain and improve hand health in such work environments. Pre-work protective or barrier creams are used and have been shown to improve hand health in manufacturing environments in which workers contact certain lubricants. Kütting, B; Baumeiseter, T; Weistenhöfer, W. Pfahlbert, A.; Uter, W. and Drexler, H., *Effectiveness of skin protection measures in prevention of occupational hand eczema*, British Journal of Dermatology (2009). Moisturizers are also recommended after exposure. While concerns based on occupational dermatitis are recognized as well as the potential for skin products to provide cost effective protection, recommendations for effective products for work environments have not been developed. Terhaer, F.; Bock, M.; Fartasch, M.; Gabard, B.; Elsner, P.; Kleesz, P; Landeck, L.; Pohrt, U.; Seyfarth, F.; Schliemann, S.; Diepgen, T; Zagrodnik, F.; and John, S., *Safety, effectiveness and comparability of professional skin cleansers*, JDDG 1610-0379, (2010).

Certain activities require use of gloves for worker protection, safe performance of work activities, or both. Exposure to harmful substances such as cleansers may require use of gloves by workers. Examples in healthcare include use of sterile gloves for surgical and certain other invasive procedures on patients. Examination gloves are indicated for direct or indirect patient contact.

One or all of worker safety, worker health and effective performance are enhanced by compliance with recommended best practices for using hand products. Recommended best practices may be based in any source. Institutions may develop recommended practices based on activities in the institution and on experience within the institution. Industry or professional associations may develop best practices that are recommended within the industry or profession. Governmental and international organizations may develop recommended practices for activities of wide concern such as those related to food safety and healthcare.

Identification of a benchmark for hand product use is an essential step in determining whether recommended practices are followed in a facility. Hand hygiene best practices may be the basis for identifying a benchmark number of hand hygiene activities that are consistent with the recommended practice. Similarly, healthcare glove use recommendations may provide the basis for the benchmark number of gloves that should be used. Benchmarks for use of pre-work creams or skin care products may also be determined based on recommended best practices. A recommended best practice may provide a benchmark based on occurrences within a facility. For example, use of gloves may indicate a need for hand hygiene or a number of cleanser uses may provide a benchmark for use of hand skin care products.

SUMMARY OF THE INVENTION

An aspect of the invention concerns assuring that workers conform to best practices for hand product use.

Another aspect of the invention concerns determining benchmark number of hand product uses based on recommended practices.

Yet another aspect of the invention concerns determining the compliance of workers with hand hygiene guidelines within a facility that requires hand hygiene.

Still another aspect of the invention concerns determining the compliance of healthcare workers with hand hygiene guidelines within a healthcare institution.

An additional aspect of the invention concerns determining the compliance of workers with hand hygiene guidelines within individual areas of a facility in which different activities that require hand hygiene occur at different locations within that facility.

Still another aspect of the invention concerns determining the compliance of healthcare workers with hand hygiene guidelines within individual areas of a healthcare institution.

Yet an additional aspect of the invention concerns determining the amount of hand hygiene activity within a facility that is consistent with hand hygiene guidelines.

Another aspect of the invention concerns determining the benchmark use of a hand product within a facility that is consistent with recommended best practices.

Yet another aspect of the invention concerns determining compliance with best practices for use of hand skin care products within a facility.

Still another aspect of the invention concerns determining compliance with that best practices for use of gloves within a facility.

DETAILED DESCRIPTION OF THE PREFERRED EMBODIMENTS

The invention concerns monitoring compliance with recommended practices for use of hand products by workers. In one aspect, the invention concerns estimating the number of hand hygiene events that should occur within an area during a period of time. In another aspect, the invention concerns estimating the number of indications for glove use. In yet another aspect, the invention concerns estimating the number of hand hygiene events and the number of indications for glove use. In still another aspect, the invention concerns estimating amount of use of skin care products. The present invention is described hereinafter by reference to the accompanying drawings and the following description that disclose embodiments of the invention. This invention may, however, be embodied in many different forms and should not be construed as limited to the embodiments set forth herein or to any aspect of that embodiment. Rather, this embodiment is an example of the invention, which has the full scope indicated by the claims.

Figure 1:
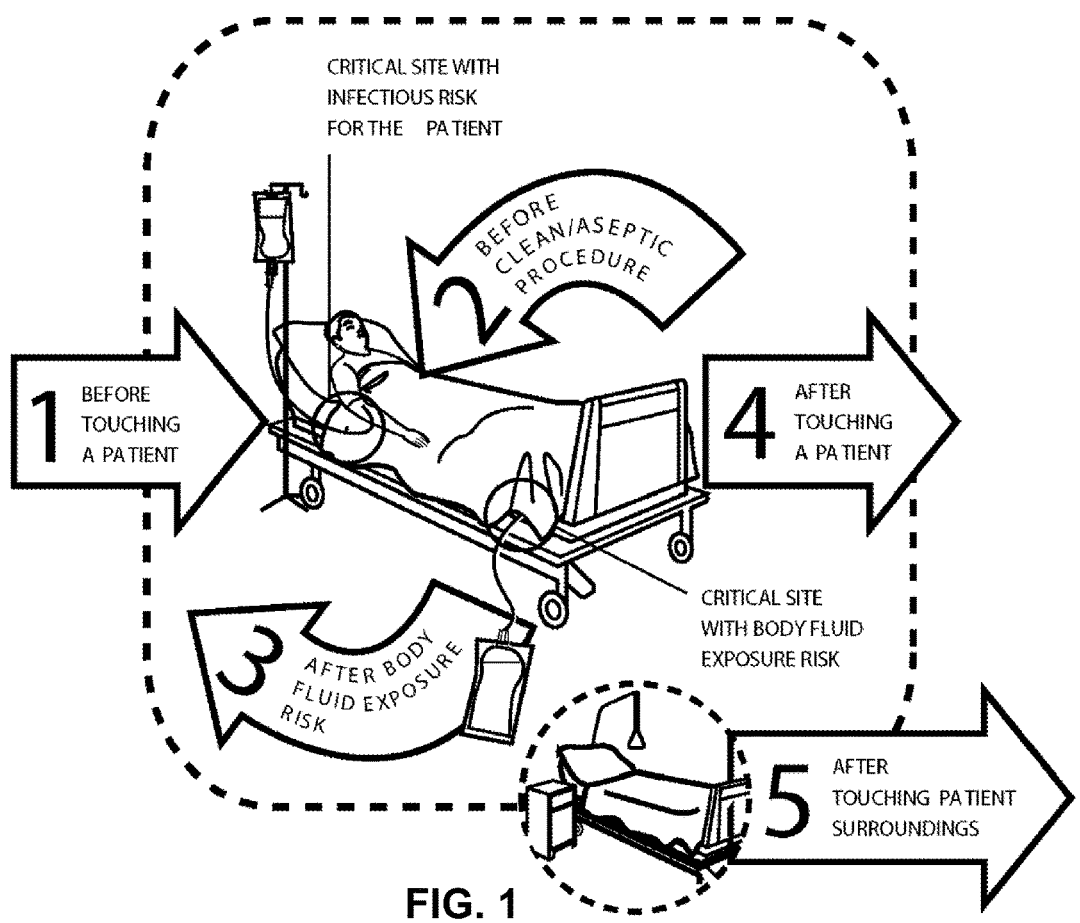
FIG. 1 is a sketch showing the five moments for hand hygiene in a healthcare setting.

The World Health Organization ("WHO") has recommended best practices for hand hygiene and glove use for healthcare. The WHO identified five moments of hand hygiene in a healthcare setting. Those five moments for hand hygiene actions are shown generally by FIG. 1 at 10. Specifically, the five moments for hand hygiene actions are before patient contact 12, before performing an aseptic task 14, after body fluid exposure risk 16, after patient contact 18 and after contact with patient surroundings 20. Hand hygiene actions can be sanitizing with a sanitizing product which does not require water or rinsing off or alternatively it can be washing with soap and water. These five moments provide guidelines for hand hygiene within a healthcare setting. The WHO has also developed recommendations for activities and circumstances under which gloves should be worn.

The Food and Drug Administration (FDA) recommends practices for hand washing for food workers. The FDA recommends that food workers should wash hands when entering a food preparation area; before putting on gloves, including between glove changes; before engaging in food preparation; before handing clean equipment and serving utensils; when changing tasks an switching between handling raw foods and working with ready to eat (RTE) foods; after handling soiled dishes, equipment, or utensils; after touching bare human body parts, for example parts other than clean hands and clean, exposed portions of arms; after using a toilet; after coughing sneezing, blowing his or her nose, using tobacco, eating, or drinking; and after caring for or handling services animals or aquatic animals such as molluscan shellfish or crustacean in display tanks. Food workers should also wash their hands after any activity that contaminates their hands. These recommendations provide bases for guidelines for hand hygiene in food facilities in which these activities occur. Other national food safety agencies similarly recommend good hand hygiene practices, including the Food Standards Agency of the United Kingdom, the European Commission, and Food Standards Australia and New Zealand.

Food safety agencies, including the FDA have developed recommendations for managing facilities based on Hazard Analysis and Critical Control Point (HACCP) systems. Hand hygiene guidelines have been included in systems that are based on HACCP analysis. HACCP is based on seven principles, the fourth of which is monitoring critical control points. Where hand hygiene is essential, HACCP principles call for monitoring of hand hygiene.

Other government, health and safety organizations have developed other recommendations for practices to prevent spread of bacteria, viruses and microorganisms within facilities. Hand hygiene guidelines can be important in clean room and sterile environments for pharmaceutical and other manufacturing for which pathogens and contaminants must be minimized. Hand hygiene is also important to maintaining safe and healthy environments. Hand hygiene recommendations for all such activities and facilities can form bases of desired best practices hand hygiene guidelines.

Worker health considerations may provide bases for best practices for use of hand skin care products within work environments. Whether hand skin care concerns are based on a work environment generally or on specific activities or exposure to specific substances, such a cleansers, hand products such as protectants, moisturizing creams and therapeutic products may be recommended to protect and enhance worker health, such as avoiding occupational dermatitis.

After developing such best practice guidelines and informing and educating workers concerning the guidelines, monitoring compliance with such guidelines is desirable to achieve the goals that the guidelines were developed to reach.

Guideline compliance is generally considered to be the number of activities that have occurred divided by the number that should have occurred. Specifically for hand hygiene, compliance is generally considered to be the number of times that hand hygiene occurs as compared to the number of times that it should occur. If a worker only washes or sanitizers his or her hands 6 out of the 10 times that they should have, they are said to exhibit a compliance rate of 60%. Similarly, glove use compliance can be characterized by the number of times that gloves are used as compared to the number of times that gloves should be used. In addition, use of gloves may be a basis for hand hygiene such as before and after wearing gloves. A composite compliance may be considered to be the number of times that hand hygiene or glove use should occur as compared to the number of times that hand hygiene and glove use should occur. Likewise, compliance with recommendations for use of a skin product may be based on the number or amount of use that occurs divided by the recommended number or amount. Use of one hand product may indicate that another product should be used, such as use of a skin care product after use of a pre-work or barrier cream or after use of gloves.

Measuring healthcare worker adherence to guidelines is not a simple matter. For hand hygiene, there are no proven standards or benchmarks that may be used. The Joint Commission on the Accreditation of Healthcare Organizations (JCAHO) requires monitoring hand hygiene compliance for accreditation yet prescribes no specific way to do so. There is a very clear need to measure hand hygiene compliance in healthcare facilities, and therefore a need to determine whether or not a hand hygiene action occurred when there was an indication for a hand hygiene action.

Measuring food worker adherence to hand hygiene guidelines is also not straightforward. While activities have been identified before which and after which a worker should wash his or her hands, methods for determining compliance with guidelines that are based on such activities have not been developed for food handling, preparing or serving activities or facilities. Similarly, other facilities in which hand hygiene is important, such as food service and processing facilities, share the need to determine whether hand hygiene benchmark guidelines are complied with. Again, there is a clear need to develop hand hygiene benchmark guidelines based on these activities for which hand hygiene is required and to measure compliance with those benchmark guidelines.

Compliance of workers with glove use guidelines is also difficult to assess. Appropriate benchmark guidelines have not been determined based on recommended circumstance under which gloves should be used that can be applied to identified activities or institutions.

Compliance of workers with guidelines for use of other skin products is subject to the same difficulties. Appropriate benchmark guidelines have not been determined based on recommended skin care product use that can be applied to identified activities or institutions.

There are a number of ways to measure compliance with recommended best practice guidelines. For hand hygiene guideline compliance, direct observation, remote observation, self-reporting and dispenser usage data or product usage data have been undertaken. Each has its own benefits and challenges.

Direct observation can determine hand hygiene compliance directly by observing both whether hand hygiene should occur and whether it does. However, direct observation is both time consuming and costly. Generally direct observation data is only collected for a small sample of the total of hand hygiene opportunities and thus has a typically low level of statistical reliability. The data is subject to bias from over or under sampling of certain shifts and units. As well, it has been shown that there are also issues regarding inter-rater (observer) reliability and therefore it is difficult to compare the results from one observer or rater with another.

Further, it has been shown that when people know they are being watched or studied there is a greater likelihood that their compliance will be higher than it would be otherwise. This is known as the Hawthorne Effect. Evidence supporting this is found in a 2009 German study that compared product usage data with direct observation data and found that the direct observation compliance rate was 2.75 times higher than that for product usage. Scheithauer S, Haefner H, Schwanz T, Schulze-Steinen H, Schiefer J, Koch A, Engels A, Lemmen S W., Compliance with Hand Hygiene on Surgical, Medical, and Neurologic Intensive Care Units: Direct Observation Versus Calculated Disinfectant Usage, Am. J. Infect. Control. 2009 December; 37(10):835-41.

Remote observation worker activity to determine guideline compliance, such as by video, can operate at any time of day or night and in any location. Remote observation is less subject to bias from over or under sampling of certain shifts and units than direct observation by an observer or rater. Remote observation is less apparent than direct observation by an observer and is therefore less likely to affect workers' practices. Data collection by remote observation is expensive because it requires installation and maintenance of the video equipment as well as the time to review the video. Remote observation can be subject to bias based on the video location within the facility. Review is subject to the same lack of inter-rater reliability as direct observation. Further, remote video observation raises privacy concerns.

Product usage is gaining acceptance by professionals as a more accurate measure of true rate of compliance with hand hygiene guidelines. In typical commercial and professional environments, hand hygiene liquids are stored and dispensed onto hands from dispensers, therefore there is a direct correlation between dispenser usage or activations and hand hygiene events being performed. Monitoring dispenser usage has the advantage of being less costly than direct or remote observation of hand hygiene. Further, dispenser usage provides an overall measure of use and it is not subject to selection bias.

There are a number of further advantages to monitoring dispenser usage. Specifically, in addition to being less costly, monitoring dispenser usage is less resource intense and therefore more efficient than observation. Dispenser usage can be monitored manually or electronically. Dispenser usage monitoring allows organization-wide trends to be tracked over time. It can be unobtrusive and designed to take up little additional space. Dispenser usage can be easily measured across all shifts, twenty-four hours a day, and seven days a week. It requires minimal staff training. Dispenser usage monitoring can easily be done in many different settings. However, dispenser usage data does not provide feedback for indications or technique. Further, it does not identify low-performing individual staff members.

In many cases, dispenser usage does not directly provide a measure of compliance as does direct observation. Dispenser usage identifies the number of times that a product has been dispensed. In the case of a hand hygiene product, dispensing indicates that hand hygiene has occurred. In the case of gloves, dispensing a pair of gloves indicates that gloves have been worn for an activity. In order to determine compliance with a guideline based on dispenser usage data, the number of times that an indicated activity, hand hygiene or glove use, should have occurred for the guideline to be complied with must be known. This number that an indicated activity should have occurred for compliance with hand hygiene guidelines is referred to as a benchmark. In cases for which use of one dispensed product indicates that another product should subsequently be used, such as use of a skin care product after use of an strong cleanser or use of skin care after use of a pre-work cream, a benchmark may be known based on the first use of a product.

In one embodiment of the present invention, a predetermined hand hygiene benchmark and hand hygiene product dispenser usage in an area of interest alone is used to calculate a compliance rate based on dispenser usage. In another embodiment, a predetermined benchmark is adjusted based on direct observation data and survey data that is relevant to the area of interest. For example in a healthcare facility, self-reported data or patient survey data may be used to provide consolidated hand hygiene information. In a healthcare facility, dispenser usage data can be used with facility and activity information to determine the product volume used per patient day or the number of times the dispenser was used per patient day.

To determine the measure of hand hygiene guideline compliance by dispenser usage, the facility being monitored is provided with a plurality of dispensers. The facility may be divided into predetermined groups of interest. The facility may be a healthcare facility including a teaching hospital, a non-teaching hospital, a long term care facility, a rehabilitation facility, a free standing surgical center, a health care professional office, a dental office, a veterinarian facility and a community care facility as well as other health care settings in which hand hygiene compliance is an important issue. The facility may be another facility in which hand hygiene is important and should be maintained such as at various stages in food preparation and service including abattoirs, preparing precooked foods and restaurants.

In order to determine compliance with hand hygiene guidelines based on dispenser usage one needs the number of hand hygiene events that actually occurred and a benchmark. The number of actual hand hygiene events and predetermined benchmark may be for a predetermined area or group and for a predetermined time. The usage may be measured for each dispenser in the predetermined group in practically real time and the captured data is transmitted electronically. The number of hand hygiene events within a predetermined time period equals a number of times the dispenser has been activated and wherein multiple activations within a predetermined activation period are considered a single dispenser usage event. It is not uncommon that when someone uses a dispensing system that rather than merely activating once, they activate the dispenser multiple times. Accordingly to accurately determine the correct number of dispenser usage events the number of times the dispenser is activated is determined. However where there are multiple activations within a predetermined activation period that is considered a single dispenser usage event. The benchmark is the number of times the dispenser should have been used for a predetermined group over a predetermined time period.

The dispenser usage compliance rate is the number of dispenser usage events divided by a benchmark. The benchmark may be particular to the predetermined group and activity of the group. To determine the benchmark for the predetermined area and time, one needs to determine the hand hygiene occurrences that should occur. For a healthcare facility, the benchmark number of hand hygiene occurrences that should occur may depend on the number of patients for the predetermined area and time and on the nature of the activity in the predetermined area.

Benchmarks for dispenser usage in a facility may be predetermined for the facility and for each area of interest in a facility by direct or remote video observation. Determining benchmarks this way is time consuming and requires significant effort. Rather than predetermine benchmarks for each facility and for each area of a facility, benchmarks are predetermined based on a selected hand hygiene guideline by observation within areas of a facility in which activities occur for which the guidelines apply. Benchmark relationships are determined between the benchmarks determined by observation and characteristics and activity of the facility. Based on these benchmark relationships, benchmarks may be predetermined for other facilities in which activities occur for which the guidelines apply based on the characteristics and activity of the other facility for which benchmark relationships have been determined.

For example, the number of hand hygiene occurrences that are consistent with the WHO five moments can be correlated with hospital conditions and activities which may include the case mix index (CMI), the ratio of the number of healthcare workers to the number of patients, and the nature of the specific unit of a healthcare facility. By use of such correlative relationships, a benchmark number of hand hygiene opportunities can be predetermined for units of a hospital based on observed numbers of hand hygiene opportunities for a different hospital.

A benchmark for a healthcare facility may be predetermined based on the number of hand hygiene events that occurred in two hospitals that were directly observed to identify the occurrences of the five moments of hand hygiene identified by the World Health Organization. One hospital was a teaching hospital and tertiary care center and the other was a community hospital. In each hospital, direct observations were made in three different types of nursing units, an adult medical-surgical intensive care unit, an adult medical inpatient ward, and an emergency department. Observations were made for all week days and all shifts during a three month period. These observations identified 6,640 hand hygiene opportunities during 436.7 hours of observations. These observations are described in more detail by "Hospital Hand Hygiene Opportunities: Where and when (HOW2)? The How2 Benchmark Study", Steed et al., Am. J. Infect. Control 2011; 39:19-26, which is incorporated herein by reference. That paper reports the number of observed hand hygiene opportunities based on each of the WHO five moments. This paper reports observation of hand hygiene opportunities, rather than observed compliance. These observations provide the number instances during the observations when hand hygiene should occur.

Figure 2:
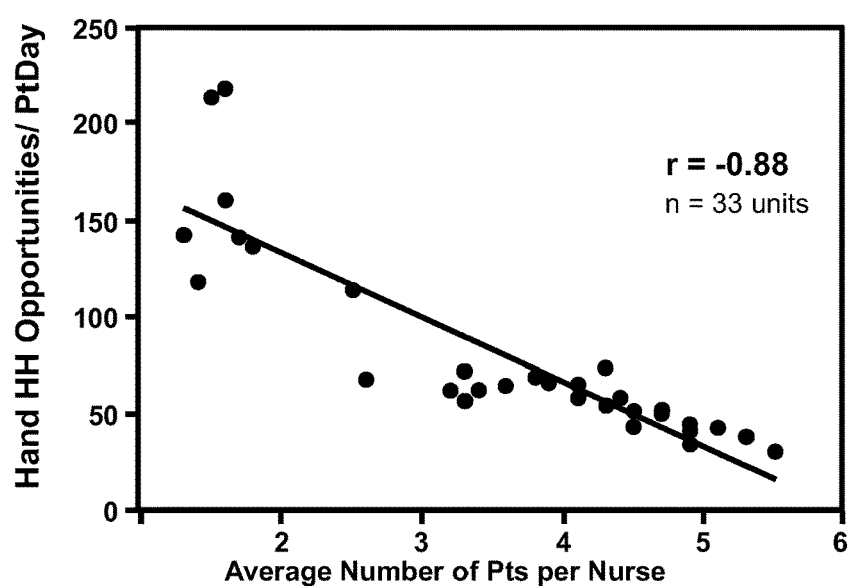
FIG. 2 is a graph of the observed number of observed hand hygiene opportunities per patient day vs. the average number of patients per nurse and a linear relationship between them based on regression analysis.

The number of times that hand hygiene should occur as shown by this data obtained by direct observation can be correlated to conditions that existed in the hospitals in which the observations were made, and can be correlated to number of occurrences of one or more of the conditions under which hand hygiene should occur. FIG. 2 shows an example of a relationship that can provide the number of hand hygiene opportunities in a hospital based on the ratio the number of patients to the number of nurses. FIG. 2 shows that a strong correlation exists between the number of hand hygiene opportunities and the average number of patients per nurse within the observed hospital units that are the basis of that graph. FIG. 2 shows a linear relationship that was determined by regression analysis between hand hygiene opportunities per patient day and the average number of patients per nurse.

The patient nurse ratio was the basis for two relationships were derived using linear regression analysis. For intensive care units, the relationship between the number of hand hygiene opportunities per patient day and the average number of patients per nurse is given by:

HH=199.01−33.03*PNR

Where

HH is the number of hand hygiene opportunities per patient day.

PNR is the average number of patients per nurse.

For non-intensive care medical units, the relationship between the number of hand hygiene opportunities per patient day and the average number of patients per nurse is given by:

HH=119.53−15.03*PNR

Where HH and PNR are as identified above. These relationships may be used to determine the denominator for determining hand hygiene compliance in ICU and non-ICU medical units.

A hand hygiene benchmark may be predetermined for a healthcare institution based on studies in which hand hygiene activities were observed and on correlations that are determined between conditions that exist in the studied institution and the observed hand hygiene activities. The identified correlations may be used to calculate a hand hygiene benchmark for a healthcare institution based on conditions in that institution. Benchmarks determined by such methods can be validated or adjusted based on observations in the healthcare institution or in a specific unit of the institution. Direct observations may be made to determine the validity of benchmarks determined by these relationships in that facility or unit. Should observations fall within the interval of twice the 95 percent confidence level, the relationship should be considered valid. If observations do not fall within that range, the relationship would be adjusted to conform to the specific unit.

Figure 3:
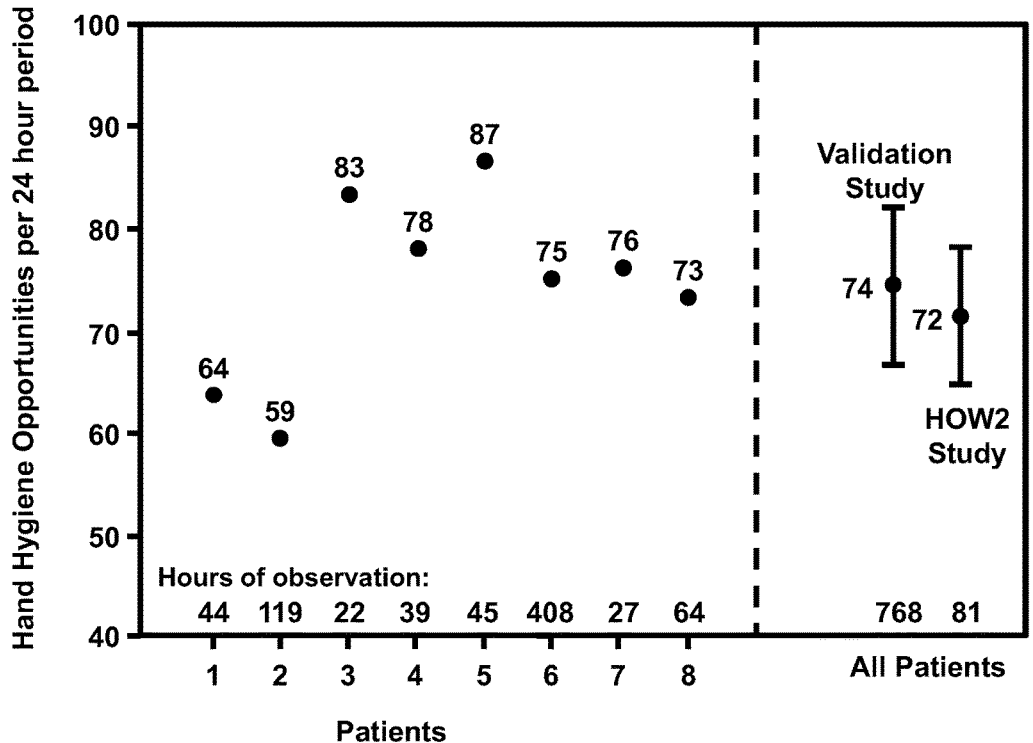
FIG. 3 is a graph of the observed number of hand hygiene opportunities per 24 hour period and a comparison showing that the video monitoring benchmark and the benchmark based on the original HOW2 study are statistically equivalent.

FIG. 3 shows the results of a validation study in which hand hygiene opportunities were observed via videotaping for eight patients and the average number of hand hygiene opportunities per 24 hour period determined. The average number of hand hygiene opportunities per 24 hour period was determined for all patient observations and compared to the prediction based on the HOW2 study referred to supra. As shown by FIG. 3, the predicted number of hand hygiene opportunities and the observed number are statistically equivalent.

Figure 4:
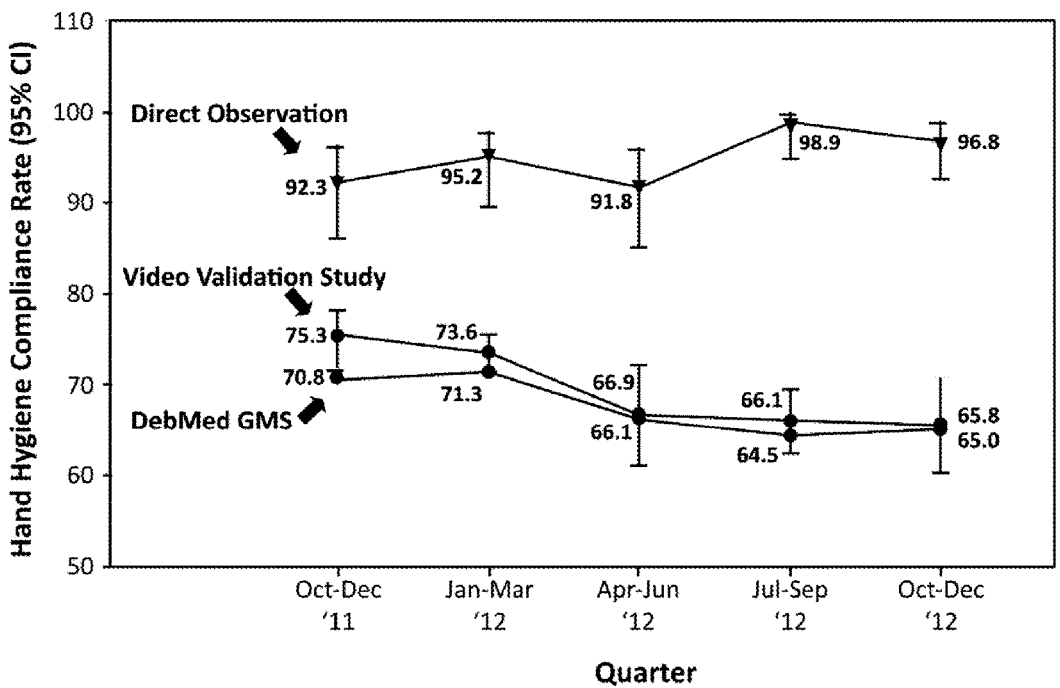
FIG. 4 is a graph of hand hygiene compliances based on direct observation, video observation and on dispenser usage utilizing a calculated benchmark.

FIG. 4 shows the observed hand hygiene compliance rates for a period of one year for thirteen patents with the 95% confidence range. FIG. 4 shows compliance rate based on dispenser usage data and calculated benchmarks (DebMed GMS), compliance rate based on video observations and compliance rate based on direct observation. As shown by FIG. 4, the hand hygiene compliance rate determined based on dispenser usage and calculated benchmark closely approximates the video observed data while the direct observation shows that direct observation overestimates compliance.

Other observed factors can be a basis for determining a hand hygiene benchmark based on direct observation data. A strong relationship has been demonstrated between the number of hand hygiene opportunities in a healthcare facility and the patient nurse ratio. As is apparent from the formulas set out above, the nature of the unit within a healthcare facility is a significant factor for the number of hand hygiene opportunities. However, the differences between healthcare institutions were not a significant factor. This relationship should therefore be appropriate for hospitals of many sizes and care levels. Such relationships may also be demonstrated for other characteristics.

Gloves use benchmarks may also be determined based on recommendations such as those of the World Health Organization. The number of uses consistent with recommendations can be observed within an institution as described for hand hygiene events. Those observed recommended uses can be characterized based on correlations to conditions and activities within the observed institution during the observations. Actual glove use is monitored by monitoring dispensing of glove from dispensers. In addition, when hand hygiene indications are based on glove use, hand hygiene benchmarks may be adjusted based on reported dispensing of gloves.

These same approaches to identifying relationships between facility characteristics and the amount of recommended activity apply to determining benchmarks for use of other hand products. Recommended use of skin care products on hands within a facility may be observed directly or indirectly. Skin care product dispenser use provides an indication that a skin care product has been used and thereby provides a measure of actual use that can be compared to a benchmark use.

Benchmarks may be determined and predetermined benchmarks may be revised as monitored use of hand products indicates that the benchmark should be adjusted. In the case of recommended use of a skin care product based on presence or use of a substance, a benchmark may be based on the presence of the substance. Providing a cleanser dispenser that reports dispensing of a cleanser provides a basis for a specific benchmark based on use of the dispensed cleanser. Use of a pre-work or barrier cream may be a basis for increasing a benchmark use of a hand washing product, and use of a hand washing product may be a basis for increasing a benchmark use of skin cream. Similarly, use of gloves may indicate a recommendation for hand hygiene or use of a skin care product or both.

It is evident that this method both determines a benchmark and the compliance rate with reasonable accuracy. The more regular the activities within a facility in which hand hygiene is a concern, the more accuracy can be expected of the benchmarks and hand hygiene compliance ratios determined by this method.

We claim:

1. A method for predetermining the benchmark number of hand product uses for a target facility comprising:
    identifying best practice recommendations for use of a hand product within a studied facility based on workers' activity within the studied facility;
    determining a study benchmark number of hand product uses for compliance in the studied facility during an observation period with the identified best practice recommendations;
    identifying studied facility characteristics of the studied facility during the observation period;
    identifying study relationships between studied facility characteristics and the study benchmark number of hand product uses;
    determining target facility characteristics for the target facility; and
    determining a benchmark number of hand product uses for the target facility for compliance with the identified best practice recommendations based on study relationships and target facility characteristics.

2. The method for predetermining the benchmark number of hand product uses for a target facility of claim 1, wherein the studied facility and the target facility are healthcare facilities.

3. The method for predetermining the benchmark number of hand product uses for a target facility of claim 2, wherein the hand product is a hand hygiene product and the best practice recommendations are recommendations for hand hygiene in a healthcare facility.

4. The method for predetermining the benchmark number of hand product uses for a target facility of claim 2, wherein the hand product is a glove and the best practice recommendations are recommendations for glove use for healthcare.

5. The method for predetermining the benchmark number of hand product uses for a target facility of claim 4, wherein the study benchmark number of hand product uses are based on one or more of the recommendations by the World Health Organization for glove use.

6. The method for predetermining the benchmark number of hand product uses for a target facility of claim 1, wherein study relationships are identified based on linear regression analysis.

7. The method for predetermining the benchmark number of hand product uses for a target facility of claim 1, wherein the studied facility and the target facility are food handling facilities.

8. The method for predetermining the benchmark number of hand product uses for a target facility of claim 7, wherein the hand product is a hand hygiene product and the best practice recommendations are recommendations for hand hygiene in a food handling facility.

9. The method for predetermining the benchmark number of hand product uses for a target facility of claim 7, wherein the hand product is a hand hygiene product and the study benchmark number of hand product uses is based on one or more of the FDA recommended circumstances when a food worker should wash his or her hands.

10. The method for predetermining the benchmark number of hand product uses for a target facility of claim 7, wherein the hand product is a glove and the best practice recommendations are recommendations for glove use during food handling.

11. A method for monitoring compliance with best practice recommendations for use of a hand product within a target facility comprising:
    identifying best practice recommendations for use of a hand product that are based on workers' activity within a target facility;
    monitoring occurrences within the target facility for which use of the hand product is recommended by the identified best practice recommendations;
    determining a benchmark use of the hand product based at least in part on the monitored occurrences;
    monitoring use of the hand product in the target facility; and
    comparing the use of the hand product in the target facility to the benchmark use in the target facility.

12. A method for monitoring compliance with best practice recommendations for use of a hand product within a target facility of claim 11, wherein the hand product is a skin care product and an occurrence that is monitored is use of a cleanser.

13. A method for monitoring compliance with best practice recommendations for use of a hand product within a target facility of claim 11 wherein:
    the hand product is a hand hygiene product; and
    an occurrence that is monitored is use of gloves.

14. A method for monitoring compliance with best practice recommendations for use of a hand product within a target facility of claim 11 wherein:
    the hand product is a hand washing product; and
    an occurrence that is monitored is use of a pre-work cream.

15. A method for monitoring compliance with best practice recommendations for use of a hand product within a target facility of claim 11 wherein:
    the hand product is a skin care product; and
    an occurrence that is monitored is use of a hand washing product.

* * * * *

UNITED STATES PATENT AND TRADEMARK OFFICE
CERTIFICATE OF CORRECTION

PATENT NO. : 10,467,718 B2
APPLICATION NO. : 13/926864
DATED : November 5, 2019
INVENTOR(S) : Paul Alper et al.

It is certified that error appears in the above-identified patent and that said Letters Patent is hereby corrected as shown below:

On the Title Page

Item (71), "Applicant:", delete "DebMed USA LLC, Charlotte NC (US)" and insert --DEB IP LIMITED, Derbyshire, United Kingdom--.

Signed and Sealed this
Tenth Day of December, 2019

Andrei Iancu
*Director of the United States Patent and Trademark Office*